United States Patent [19]

Kottwitz et al.

[11] Patent Number: 5,380,917
[45] Date of Patent: Jan. 10, 1995

[54] PROCESS FOR THE PRODUCTION OF BENZOYLOXYBENZENE SULFONATES

[75] Inventors: Beatrix Kottwitz; Harald Kuester; Andrea Berger, all of Duesseldorf, Germany

[73] Assignee: Henkel Kommanditgesellschaft auf Aktien, Duesseldorf, Germany

[21] Appl. No.: 108,652

[22] Filed: Aug. 31, 1993

[30] Foreign Application Priority Data

Mar. 4, 1991 [DE] Germany ............... 4106843

[51] Int. Cl.$^6$ ............................... C07C 69/76
[52] U.S. Cl. ................................. 560/109
[58] Field of Search ......................... 560/109

[56] References Cited

U.S. PATENT DOCUMENTS

| 4,908,471 | 2/1990 | Sankey et al. | 560/109 |
| 5,274,172 | 12/1993 | Chou et al. | 560/109 |

FOREIGN PATENT DOCUMENTS

| 0120591 | 10/1984 | European Pat. Off. . |
| 0148148 | 7/1985 | European Pat. Off. . |
| 0294073 | 12/1988 | European Pat. Off. . |
| 0638072 | 11/1936 | Germany . |
| 8202896 | 9/1982 | WIPO . |

*Primary Examiner*—José G. Dees
*Assistant Examiner*—Samuel Barts
*Attorney, Agent, or Firm*—Ernest G. Szoke; Wayne C. Jaeschke; Henry E. Millson, Jr.

[57] ABSTRACT

Process for the production of a benzoyloxybenzene sulfonate by reaction of a phenol sulfonate with an optionally substituted benzoyl chloride in the presence of a base, wherein the reaction is carried out in a solvent mixture consisting of water and an organic solvent which is ethanol, isopropanol, dioxane, tetrahydrofuran, or mixtures thereof.

20 Claims, No Drawings

PROCESS FOR THE PRODUCTION OF BENZOYLOXYBENZENE SULFONATES

BACKGROUND OF THE INVENTION

1. Field of the Invention

This invention relates to a process for the production of phenol esters which, in recent years, have acquired interest as activators for inorganic peroxy compounds, particularly where they are used as bleaching agents.

2. Statement of Related Art

Acyloxybenzene sulfonates can be produced from the phenol sulfonates by reaction with the corresponding anhydrides either in the absence of solvents or in suitable solvents. However, the higher anhydrides are relatively expensive and the reaction mixture is difficult to work up. Accordingly, the reaction of phenol sulfonates with the corresponding acid chlorides is more common. European patent application 120 591 describes this reaction in anhydrous organic solvents, such as chlorobenzene. However, difficulties are involved in removal of the HCl released or NaCl (after addition of base). Where excess acid chloride is used as the solvent, as proposed in European patent application 148 148, removal of the end product in pure form involves certain problems. In addition, it is necessary in all these proposals to use strictly anhydrous reagents and solvents and to carry out the acylation reaction in the absence of moisture. An alternative reaction with, basically, more favorable prospects is the Schotten-Baumann acylation proposed for these compounds in European patent application 294 073. In the Schotten-Baumann acylation, base, phenol sulfonate and a small quantity of a surfactant are dissolved in water and benzoyl chloride is subsequently added dropwise to the resulting solution. However, the acylation reaction has to be carried out in a relatively narrow temperature range and separation of the end product in high yields is only possible if the reaction is subsequently cooled to temperatures in the range from about 0° to 5° C. To avoid contamination by relatively large quantities of the corresponding carboxylic acid, surfactant has to be added. Working up on an industrial scale is complicated above all by the need to cool the reaction mixture as a whole to isolate the end product and to wash the end product, even at low temperatures, and also by addition of the surfactant.

DESCRIPTION OF THE INVENTION

In the course of efforts to improve the Schotten-Baumann synthesis, it was found that the disadvantages described above could be avoided if, instead of water, a mixture of water and certain organic solvents was used as the reaction medium.

Accordingly, the present invention relates to a process for the production of benzoyloxybenzene sulfonates by reaction of phenol sulfonate with optionally substituted benzoyl chloride in the presence of base, characterized in that the reaction is carried out in a solvent mixture consisting of water and an organic solvent from the group consisting of ethanol, isopropanol, dioxane, tetrahydrofuran and mixtures thereof. The ratio by weight of water to organic solvent in this solvent mixture is preferably 6:1 to 1:1.6 and more preferably 4:1 to 1.1:1.

In the new process, the reaction mixture no longer has to be cooled on completion of the acylation, instead the end product can be filtered off at the actual reaction temperature and preferably slightly below that temperature, more particularly at temperatures between room temperature and around 50° C., without any significant losses of yield. Even if no surfactant is added to the reaction mixture, the end product contains at most traces of benzoic acid and phenol sulfonate.

The starting materials for the process according to the invention may be varied within relatively wide limits. The phenol sulfonates are the salts of phenol sulfonic acids (hydroxybenzene sulfonic acids) which are introduced as such into the reaction or are prepared from a sufficient quantity of base and the free phenol sulfonic acids before the beginning of the acylation. The hydroxy group and the sulfonate group may be in the ortho, meta or para position to one another. The phenol ring may optionally bear other substituents. However, unsubstituted p-phenol sulfonate, particularly the sodium salt, is preferably used.

The preferred reactant for the phenol sulfonate is the chloride of the unsubstituted benzoic acid, benzoyl chloride. If desired, substituted benzoyl chlorides may also be used instead of benzoyl chloride itself, for example if substituted perbenzoic acids are to be formed in the subsequent use of the reaction product as a peroxide activator. The benzoyl chlorides substituted by methyl or chlorine in the ortho, meta or para position are mentioned by way of example in this regard. The benzoyl chloride is normally introduced into the reaction in a stoichiometric quantity or in a slight molar excess, based on phenol sulfonate. The molar ratio of acid chloride to phenol sulfonate is preferably between 1.1:1 and 1:1.

The function of the base added during the acylation reaction is to accelerate the reaction through formation of the phenolate and to bind the HCl released in salt form. In principle, any sufficiently strong bases are suitable. However, alkali metal hydroxides, such as NaOH and KOH, tertiary amines, such as triethanolamine, and inorganic salts showing an alkaline reaction, such as $Na_2CO_3$ and $K_2CO_3$, are preferably used. Normally, at least one equivalent base is used per mol phenol sulfonate. Where alkali metal hydroxides, particularly KOH, are used, the molar ratio of base to phenol sulfonate is preferably between 1.2:1 and 1:1; where alkali metal carbonates are used, the molar ratio of base to phenol sulfonate is preferably between 2.8:1 and 1:2. The particularly preferred base for the process according to the invention is potassium carbonate.

To carry out the process, a solution or suspension of base and phenol sulfonate in the solvent mixture is initially prepared. The individual constituents may be added in any order. For example, a solution of the base in water may be initially prepared, the organic solvent subsequently added and, lastly, the phenol sulfonate stirred in. The ratio by weight of water to phenol sulfonate in this mixture is preferably between 1:1 and 10:1 and more preferably between 1.25:1 and 8:1. The necessary quantity of benzoyl chloride is then introduced into this mixture at room temperature or at a slightly elevated temperature, preferably not exceeding 50° C., for example at the same rate at which the benzoyl chloride reacts off, the reaction mixture optionally having to be cooled to ensure that the temperature does not exceed 50° C. and preferably 40° C. After the addition, the reaction mixture is stirred until all the acid chloride has reacted off. The end product precipitated is then filtered off and, where necessary, washed with a mixture of water and organic solvent. In general, this solvent mixture has the same composition as in the reaction mixture, although it may also differ from that mixing ratio. Finally, the product is suitably freed from adhering solvent by drying. It may be tested for impurities (benzoic acid and phenol sulfonate) by potentiometric acid/base titration.

As known in principle for phenol esters, the product of the process according to the invention may be used as an activator for inorganic peroxy compounds. For example, the bleaching performance of inorganic peroxy compounds in detergents can be improved or the disinfecting performance of disinfectants increased by activation in this way. Accordingly, the present invention also relates to the above-mentioned use of the benzoyloxybenzene sulfonates produced in accordance with the invention..

EXAMPLES

1. Synthesis of benzoyloxybenzene sulfonate 33.2 g (0.24 mol) potassium carbonate were dissolved in 120 ml water. After addition of 100 ml isopropanol, 92.8 g (0.4 mol) p-hydroxybenzene sulfonic acid sodium salt dihydrate were suspended in the mixture. 72.7 g (0.517 mol) benzoyl chloride were then added dropwise with stirring over a period of 30 minutes at 32° C., after which the mixture was stirred for 1 hour at 32° C. Without cooling the reaction mixture, the solid precipitated was then filtered off and washed twice with 10 ml of a solvent mixture. After drying in vacuo at 30 to 40° C., the yield amounted to 108.5 g (90.3% of the theoretical). According to potentiometric titration, the product was free from benzoic acid and unreacted phenol sulfonate.

2. Synthesis of benzoyloxybenzene sulfonate

The process corresponded to Example 1, except that the reaction mixture was kept at 40° C. before filtration. The yield amounted to 107.4 g (89.4% of the theoretical) for the same purity.

3. Synthesis of 3-chlorobenzoyloxybenzene sulfonate 16.6 g (0.12 mol) potassium carbonate were dissolved in 60 ml water. After addition of 50 ml isopropanol, 46.4 g (0.2 mol) sodium p-phenol sulfonate dihydrate were suspended in the solution. The 3-chlorobenzoyl chloride (38.5 g=0.22 mol) was added over a period of 30 minutes at a reaction temperature of 20° to 25° C. While the reaction mixture was stirred for another hour at room temperature, the end product crystallized out from the initially clear solution. It was filtered off and washed with 10 ml isopropanol. After drying in vacuo, the yield amounted to 65 g (phenol sulfonate content 3%), corresponding to a yield of 94% of the theoretical.

4. Synthesis of 2,4-dichlorobenzoyloxybenzene sulfonate

The procedure was as described in Example 3, except that 46.1 g (0.22 mol) 2,4-dichlorobenzoyl chloride were used instead of 3-chlorobenzoyl chloride. The yield amounted to 72.5 g (dichlorobenzoic acid content 1.7%), corresponding to 96.5% of the theoretical.

We claim:

1. In a process for the production of a benzoyloxybenzene sulfonate by reaction of a phenol sulfonate with optionally substituted benzoyl chloride in the presence of a base, the improvement wherein the reaction is carried out in a solvent mixture consisting essentially of water and an organic solvent selected from the group consisting of ethanol, isopropanol, dioxane, tetrahydrofuran, and mixtures thereof.

2. The process of claim 1 wherein the solvent mixture contains water and organic solvent in a ratio of 6:1 to 1:1.6.

3. The process of claim 2 wherein said ratio is 4:1 to 1.1:1.

4. The process of claim 1 wherein the organic solvent is isopropanol.

5. The process of claim 1 wherein the ratio by weight of water to phenol sulfonate in the reaction mixture is from 1:1 to 10:1.

6. The process of claim 5 wherein said ratio is from 1.25:1 to 8:1.

7. The process of claim 1 wherein the optionally substituted benzoyl chloride and phenol sulfonate are present in a molar ratio of from 1.1:1 to 1:1.

8. The process of claim 1 wherein the phenol sulfonate is a sodium salt.

9. The process of claim 8 wherein the phenol sulfonate is phenol sulfonate.

10. The process of claim 1 wherein the base is an alkali metal hydroxide, a tertiary amine, or an alkaline inorganic salt.

11. The process of claim 9 wherein the base is an alkali metal hydroxide and the molar ratio of base to phenol sulfonate is from 1.2:1 to 1:1.

12. The process of claim 1 wherein the base is $K_2CO_3$ and the molar ratio of base to phenol sulfonate is from 2.8:1 to 1:2.

13. The process of claim 1 wherein the solvent mixture contains water and organic solvent in a ratio of 4:1 to 1.1:1; the ratio by weight of water to phenol sulfonate in the reaction mixture is from 1:1 to 10:1; and the optionally substituted benzoyl chloride and phenol sulfonate are present in a molar ratio of from 1.1:1 to 1:1.

14. The process of claim 13 wherein the ratio by weight of water to phenol sulfonate is from 1.25:1 to 8:1; and the base is an alkali metal hydroxide, a tertiary amine, or an alkaline inorganic salt.

15. A process for the production of a benzoyloxybenzene sulfonate comprising the steps of
A) forming a solution or suspension of a phenol sulfonate and a base in a solvent mixture consisting essentially of water and an organic solvent selected from the group consisting of ethanol, isopropanol, dioxane, tetrahydrofuran, and mixtures thereof;
B) adding to the solution or suspension from step A) an optionally substituted benzoyl chloride at a reaction temperature not exceeding 50° C.;
C) mixing the reaction mixture from step B) at said reaction temperature until substantially all of said benzoyl chloride has reacted; and
D) isolating the resulting benzoyloxybenzene sulfonate from the reaction mixture.

16. The process of claim 15 wherein step D) is carried out by filtering off said sulfonate from the reaction mixture.

17. The process of claim 15 wherein step D) is carried out at or near the reaction temperature in step B).

18. The process of claim 15 wherein in step A) the solvent mixture contains water and organic solvent in a ratio of 4:1 to 1.1:1; the ratio by weight of water to phenol sulfonate in the reaction mixture is from 1:1 to 10:1; and in step B) the optionally substituted benzoyl chloride and phenol sulfonate are in a molar ratio of from 1.1:1 to 1:1.

19. The process of claim 18 wherein the ratio by weight of water to phenol sulfonate is from 1.25:1 to 8:1; and the base is an alkali metal hydroxide, a tertiary amine, or an alkaline inorganic salt.

20. The process of claim 19 wherein the base is an alkali metal carbonate and the molar ratio of base to phenol sulfonate is from 2.8:1 to 1:2.

* * * * *